United States Patent
Smith

(10) Patent No.: US 10,436,734 B2
(45) Date of Patent: Oct. 8, 2019

(54) CAPACITIVE SENSOR ARRAY FOR STRUCTURE DAMAGE DETECTION OR HEALTH ASSESSMENT

(71) Applicant: The Boeing Company, Chicago, IL (US)

(72) Inventor: Robert A. Smith, Hampton Cove, AL (US)

(73) Assignee: The Boeing Company, Chicago, IL (US)

( * ) Notice: Subject to any disclaimer, the term of this patent is extended or adjusted under 35 U.S.C. 154(b) by 144 days.

(21) Appl. No.: 15/624,867

(22) Filed: Jun. 16, 2017

(65) Prior Publication Data

US 2018/0364189 A1 Dec. 20, 2018

(51) Int. Cl.
*G01R 27/26* (2006.01)
*G01N 27/24* (2006.01)
*G01N 27/22* (2006.01)
*G01R 17/16* (2006.01)

(52) U.S. Cl.
CPC .............. *G01N 27/24* (2013.01); *G01N 27/22* (2013.01); *G01N 27/221* (2013.01); *G01N 27/226* (2013.01); *G01N 27/228* (2013.01); *G01R 17/16* (2013.01); *G01R 27/26* (2013.01); *G01R 27/2605* (2013.01)

(58) Field of Classification Search
CPC .... G01N 27/22; G01N 27/221; G01N 27/226; G01N 27/228; G01R 27/2605; G01R 27/26; G01R 17/16
USPC ... 324/76.11–76.83, 459, 600, 649, 658, 663
See application file for complete search history.

(56) References Cited

U.S. PATENT DOCUMENTS

| | | | |
|---|---|---|---|
| 2008/0216898 A1* | 9/2008 | Grant | A61M 1/1037 137/154 |
| 2008/0217049 A1* | 9/2008 | Dudnikov | H01G 4/06 174/260 |
| 2008/0273311 A1* | 11/2008 | Biunno | H05K 1/162 361/748 |

OTHER PUBLICATIONS

Gonzalez, Gabriel et al., Design and Fabrication of Interdigital Nanocapacitors Coated with HfO2, Sensors 2015, Jan. 16, 2015.

* cited by examiner

*Primary Examiner* — Giovanni Astacio-Oquendo
*Assistant Examiner* — Raul J Rios Russo
(74) *Attorney, Agent, or Firm* — McDonnell Boehnen Hulbert & Berghoff LLP

(57) ABSTRACT

An example system includes an array of capacitive elements, a measurement lead, and a ground plane lead. One or more respective capacitive elements of the array of capacitive elements include a dielectric substrate and a corresponding top conductive layer, with each dielectric substrate configured to be positioned between the top conductive layer and a common ground plane. The measurement lead is coupled to the top conductive layer of each of the one or more respective capacitive elements. The ground plane lead is configured to be coupled to the common ground plane. The capacitive elements are structured such that the capacitive elements have varying respective capacitances, and the capacitive elements are arranged positionally within the array of capacitive elements such that a change in total capacitance is indicative of damage to a particular capacitive element at a particular position within the array of capacitive elements.

20 Claims, 11 Drawing Sheets

MEASURING THE BASELINE TOTAL CAPACITANCE OF THE ARRAY OF CAPACITIVE ELEMENTS — 1012

FIG. 11

REFERRING TO A CAPACITANCE VARIATION DATA STRUCTURE TO DETERMINE THE PARTICULAR CAPACITIVE ELEMENT CORRESPONDING TO THE DETERMINED DIFFERENCE, WHEREIN THE CAPACITANCE VARIATION DATA STRUCTURE CORRELATES CAPACITANCE VARIATIONS TO INDIVIDUAL CAPACITIVE ELEMENTS OF THE ARRAY OF CAPACITIVE ELEMENTS — 1014

FIG. 12

WIRELESSLY COMMUNICATING THE INDICATION TO ANOTHER DEVICE — 1016

FIG. 13

CAPACITIVE SENSOR ARRAY FOR STRUCTURE DAMAGE DETECTION OR HEALTH ASSESSMENT

FIELD

The present disclosure relates generally to structural health assessment, and more particularly, to systems and methods for assessing structural health or detecting structural damage using an array of capacitive elements.

BACKGROUND

The ability to assess the structural health of a structure is useful in various situations. By way of example, the ability to detect damage to surfaces of aircrafts and other moving platforms is useful to operators of such platforms. Similarly, the ability to assess the structural health of sections of bridges and other types of infrastructure is useful to civil engineers or other interested parties.

Sensing damage to complex or large surfaces in real-time is challenging for existing sensor systems. Existing sensor systems may be overly bulky, may add excessive weight to a structure, and may not be energy efficient. Further, it may be difficult to integrate existing sensor systems into complex or large structures. Improvements are therefore desired.

SUMMARY

In one example, a system configured to detect in-situ structural damage is described. The system includes an array of capacitive elements, a measurement lead, and a ground plane lead. One or more respective capacitive elements of the array of capacitive elements include a dielectric substrate and a corresponding top conductive layer, with each dielectric substrate configured to be positioned between the top conductive layer and a common ground plane. The measurement lead is coupled to the top conductive layer of each of the one or more respective capacitive elements. The ground plane lead is configured to be coupled to the common ground plane. The capacitive elements of the array of capacitive elements are structured such that the capacitive elements have varying respective capacitances. In addition, the capacitive elements of the array of capacitive elements are arranged positionally within the array of capacitive elements such that a change in total capacitance between the measurement lead and the ground plane lead is indicative of damage to a particular capacitive element at a particular position within the array of capacitive elements.

In another example, a system configured to detect in-situ structural damage is described. The system includes an array of capacitive elements, a measurement lead coupled to each of the capacitive elements of the array of capacitive elements, and a ground plane lead coupled to each of the capacitive elements of the array of capacitive elements. The capacitive elements of the array of capacitive elements are structured such that the capacitive elements have varying respective capacitances. In addition, the capacitive elements of the array of capacitive elements are arranged positionally within the array of capacitive elements such that a change in total capacitance between the measurement lead and the ground plane lead is indicative of damage to a particular capacitive element at a particular position within the array of capacitive elements.

In another example, a method for detecting in-situ structural damage is described. The method includes applying a flexible sensor to a surface of a structure, the flexible sensor including an array of capacitive elements having varying respective capacitances. The method also includes measuring a total capacitance of the array of capacitive elements. Further, the method includes determining a difference between the measured total capacitance of the array of capacitive elements and a baseline total capacitance of the array of capacitive elements. Still further, the method includes determining, using a computing device and based on the determined difference, a particular capacitive element exhibiting a capacitance variation, and providing an indication of a position of the particular capacitive element within the flexible sensor.

The features, functions, and advantages that have been discussed can be achieved independently in various examples or may be combined in yet other examples further details of which can be seen with reference to the following description and figures.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying figures, wherein:

FIG. 11 shows a flowchart of another example method for use with the method shown in FIG. 10, according to an example embodiment.

FIG. 12 shows a flowchart of another example method for use with the method shown in FIG. 10, according to an example embodiment.

FIG. 13 shows a flowchart of another example method for use with the method shown in FIG. 10, according to an example embodiment.

DETAILED DESCRIPTION

Figure 1:
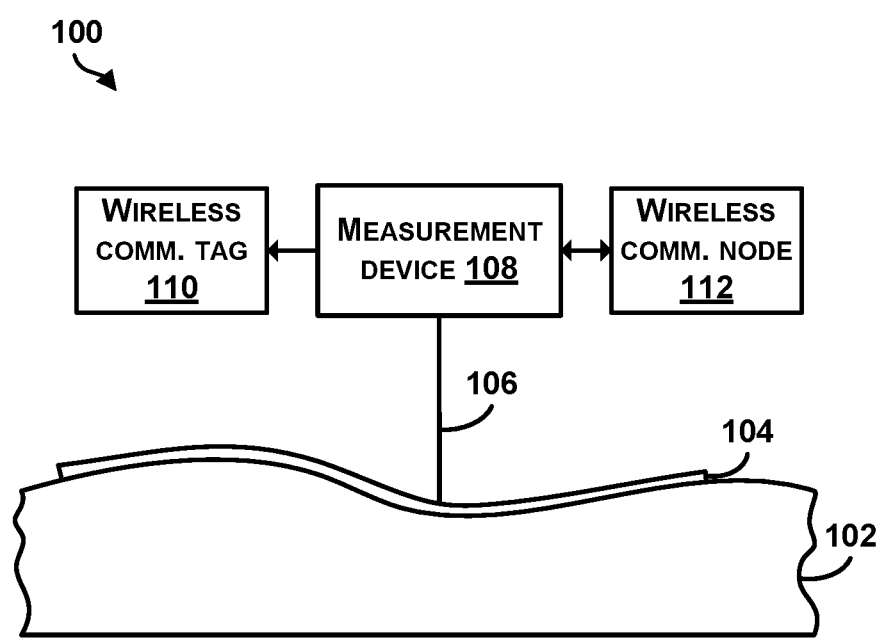
FIG. 1 illustrates an example system, according to an example embodiment.

Disclosed examples will now be described more fully hereinafter with reference to the accompanying figures, in which some, but not all of the disclosed examples are shown. Indeed, several different examples may be provided and should not be construed as limited to the examples set forth herein. Rather, these examples are provided so that this disclosure will be thorough and complete and will fully convey the scope of the disclosure to those skilled in the art.

Described herein are systems and methods for detecting structural damage or assessing structural health using an array of capacitive elements. One example system includes an array of capacitive elements, a measurement lead coupled to each of the capacitive elements, and a ground plane lead coupled to each of the capacitive elements. The capacitive elements of the array of capacitive elements are structured such that the capacitive elements have varying respective capacitances. The capacitive elements of the array of capacitive elements are also arranged positionally within the array of capacitive elements such that a change in total capacitance between the measurement lead and the ground plane lead is indicative of damage to a particular capacitive element at a particular position within the array of capacitive elements.

As described further below, the array of capacitive elements can be applied to complex structures of various sizes, and may provide a means to assess structural health and detect damage to such structures in real-time. The array of capacitive elements may be part of a system that is configured to be applied on a surface of a structure, with the array of capacitive elements spread out over the surface of the structure such that the change in total capacitance is indicative of damage to a particular position of the surface of the structure.

In some cases, when the array of capacitive elements is installed on a structure, a measurement device may determine a baseline total capacitance for the array. Subsequently, the measurement device may obtain measurements of the total capacitance of the array to assess structural health of the structure and monitor for damage to the structure. If the measured total capacitance does not deviate substantially from the baseline total capacitance, an operator of the system may interpret the measured total capacitance as an indication that the structural health of the structure has not decreased. On the other hand, if damage to the structure occurs, one of the capacitive elements may exhibit a capacitance variation such that the measured total capacitance varies from the baseline total capacitance. Based on a difference between the measured total capacitance and the baseline total capacitance, the capacitive element exhibiting the capacitance variation can be identified. Additionally, the location of the capacitive element with respect to the structure can be identified to pinpoint a damaged area on the structure.

In some examples, the capacitive elements of the array of capacitive elements may be arranged in a row/column matrix, and be electrically connected in series and parallel combinations. Each capacitive element can have a different shape, construct, or size, so that the capacitive elements of the array of capacitive elements have unique, respective capacitances.

Further, the array of capacitive elements can be fabricated using flexible hybrid electronic approaches such that the material layers are flexible and/or stretchable, and can adhere to complex structures, such as simple concave or convex surfaces, folded or sharp edge interfaces, etc. In one example, the array of capacitive elements may be provided on a flexible sensor that can be attached to an outer surface of a structure. In another example, the array of capacitive elements may be embedded within a structure. For instance, an array of capacitive elements may be embedded beneath an outer layer of a structure.

Advantageously, the systems described herein are scalable to provide damage detection or health assessment over large areas of a structure. For instance, multiple individual arrays of capacitive elements may be interconnected to form a larger array of capacitive elements. With this configuration, each of the individual arrays may be coupled to a measurement device that can distinguish between the multiple arrays, and localized damage within the individual arrays.

The systems and methods can be applied to structures to detect in-situ structural damage. That is to say, the systems and methods can detect damage to a structure or assess the structural health of a structure while the structure is positioned in its natural position and without being moved to another position, or while the structure is operated in its natural environment. Examples of structural damage include deformation, degradation, moisture intrusion, corrosion, and delamination, among other types of damage.

Various other features of these systems and methods are described hereinafter with reference to the accompanying figures.

Referring now to FIG. 1, an example system 100 is illustrated. In particular, FIG. 1 illustrates an example system 100 for detecting in-situ structural damage to a structure 102. By way of example, the structure 102 may be a moving platform, such as an aircraft or terrestrial vehicle. Alternatively, the structure 102 may be a bridge, tunnel, or other type of infrastructure.

As further shown in FIG. 1, the example system 100 includes a flexible sensor 104, a measurement lead 106, a measurement device 108, a wireless communication tag 110, and a wireless communication node 112.

In one example, the flexible sensor 104 may be a flexible hybrid electronic applique sensor that can adhere to a surface of the structure 102 or be embedded into the structure 102. The flexible sensor 104 may be fabricated using additive and subtractive manufacturing processes. As described further below, the flexible sensor 104 may include an array of capacitive elements (not shown in FIG. 1). When the flexible sensor is attached to the surface of the structure 102, the array of capacitive elements may be spread out over the surface of the structure such that a change in total capacitance of the array of capacitive elements is indicative of damage to a particular position of the surface of the structure 102.

The measurement device 108 is coupled to the flexible sensor 104 via the measurement lead 106. The measurement device 108 may be or include a controller or similar computing device that may be configured to perform the various measurement functions described herein. By way of example, the measurement device 108 may be configured to measure changes in total capacitance of the array of capacitive elements of the flexible sensor 104. For instance, the measurement device 108 may be configured to measure a baseline total capacitance, measure a current total capacitance, and determine a difference between the current total capacitance and the baseline total capacitance. The measurement device 108 may also be configured to determine, based on the determined difference, a particular capacitive element exhibiting a capacitance variation, and provide an indication of a position of the particular capacitive element within the flexible sensor 104.

The measurement device 108 may include at least one processor. The processor may be any type of processor, such as a microprocessor, digital signal processor, multicore processor, etc., coupled to a memory. The measurement device 108 may also include hardware to enable communication within the measurement device 108 and between the measurement device 108 and one or more other devices, such as the wireless communication tag 110 or wireless communication node 112.

The wireless communication tag 110 may be configured to receive data from the measurement device 108, store the received data, and transmit the received data to another device. In one example, the wireless communication tag 110 may be a radio frequency identification (RFID) tag that can be read or interrogated by an RFID reader. For instance, the RFID tag may store an indication of a total capacitance of an array of capacitive elements, which can then be read by the RFID reader. Alternatively, the RFID tag may store an indication of a particular capacitive element exhibiting a capacitance variation. Accordingly, the wireless communication tag 110 may include an integrated circuit and an antenna.

The wireless communication node 112 may be configured to receive data from the measurement device 108 and facilitate wireless communication with one or more other devices. The wireless communication node 112 may support one-way or two-way wireless communication with the other device, and may operate in accordance with one or more wireless communication protocols, such as one or more IEEE 801.11 standards, ZigBee standards, Bluetooth standards, etc. In one example, the wireless communication node 112 may receive an indication of a total capacitance of an array of capacitance elements, and wirelessly communicate an indication of the total capacitance to another device. The wireless communication node 112 may periodically transmit the indication to another device. Additionally or alternatively, the wireless communication node 112 may communicate the indication of the total capacitance to another device in response to receiving a request from the other device. In some examples, instead of or in addition to communicating the indication of the total capacitance, the wireless communication node 112 may communicate an indication of a particular capacitive element exhibiting a capacitance variation.

Figure 2:
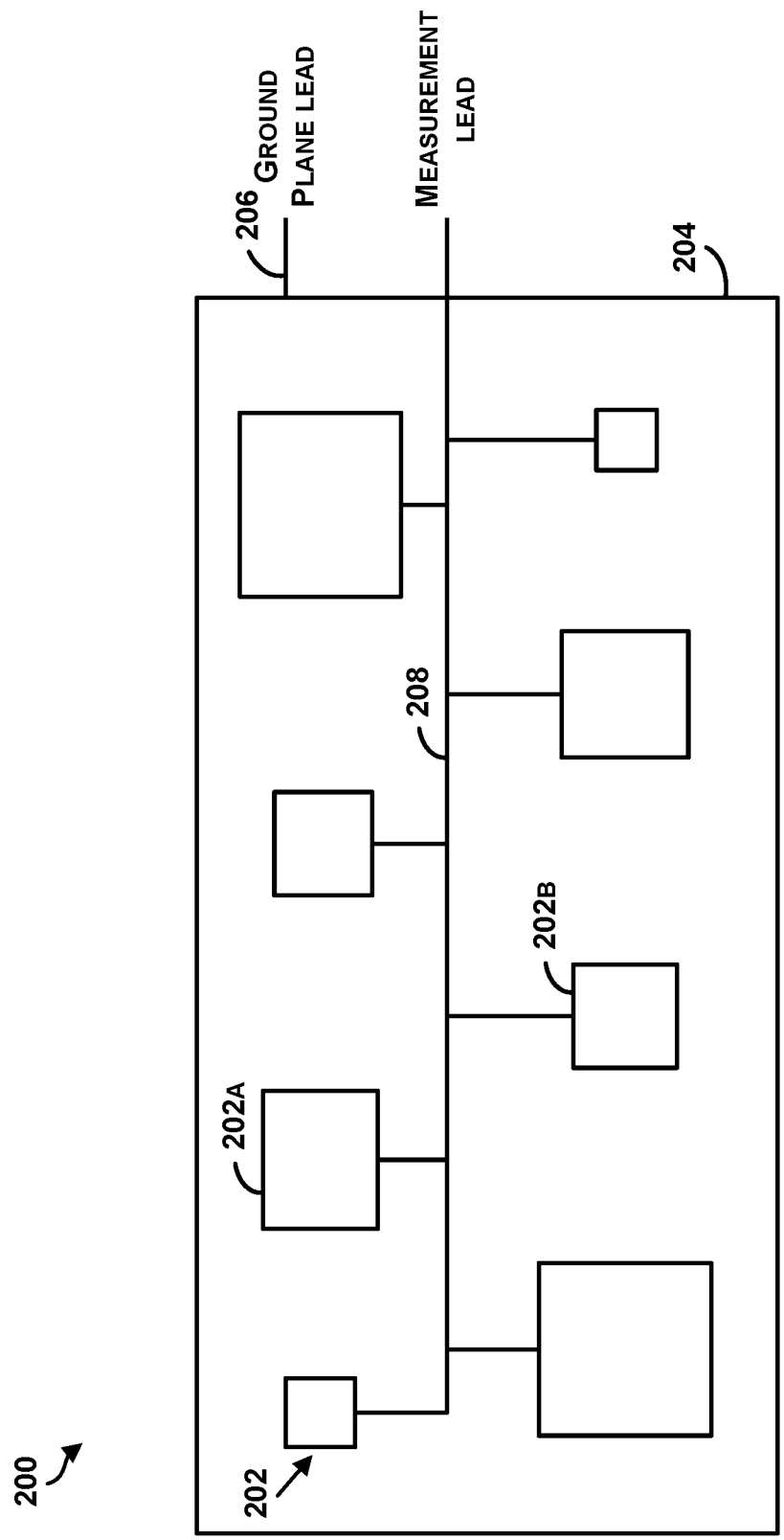
FIG. 2 illustrates an example sensor, according to an example embodiment.

FIG. 2 illustrates an example sensor 200. The sensor 200 may represent the flexible sensor 104 of FIG. 1. As shown in FIG. 2, the sensor 200 includes an array of capacitive elements 202, a common ground plane 204, a ground plane lead 206, and a measurement lead 208.

The capacitive elements 202 are arranged in a row/column matrix. In particular, the capacitive elements 202 are arranged in two rows, with each row having four capacitive elements.

The capacitive elements of the array of capacitive elements 202 are structured such that the capacitive elements have varying respective capacitances. As illustrated in FIG. 2, the capacitive elements have varying geometric areas such that the capacitive elements have varying respective capacitances. For instance, a first capacitive element 202a has a larger geometric area than a second capacitive element 202b. As such, assuming the first capacitive element 202a and the second capacitive element 202b are the same type of capacitive element, the first capacitive element 202a has a larger capacitance than the second capacitive element 202b.

In one example, the respective capacitances of the capacitive elements from left to right in the top row may be 5 picofarads, 12 picofarads, 8 picofarads, and 20 picofarads, and the respective capacitances of the capacitive elements from left to right in the bottom row may be 30 picofarads, 10 picofarads, 15 picofarads, and 3 picofarads. As described further below, the differing capacitances of the capacitive elements 202 allow a measurement device to locate a capacitive element that is exhibiting a capacitance variation.

Each of the capacitive elements 202 is coupled to the common ground plane 204, which in turn is coupled to the ground plane lead 206. In one example, the common ground plane 204 may be a metallic surface of a structure that the sensor 200 is attached to. In another example, the common ground plane 204 may be a separate metallic surface. For instance, the capacitive elements 202 may be fabricated on a flexible substrate, and the common ground plane 204 may be a metallic surface that is attached beneath the flexible substrate.

Each of the capacitive elements 202 is also coupled to the measurement lead 208. In one example, the measurement lead 208 may be printed on the sensor 200 as a flat conductor. For instance, the measurement lead 208 may be printed with a flexible conductive ink.

Figure 3:
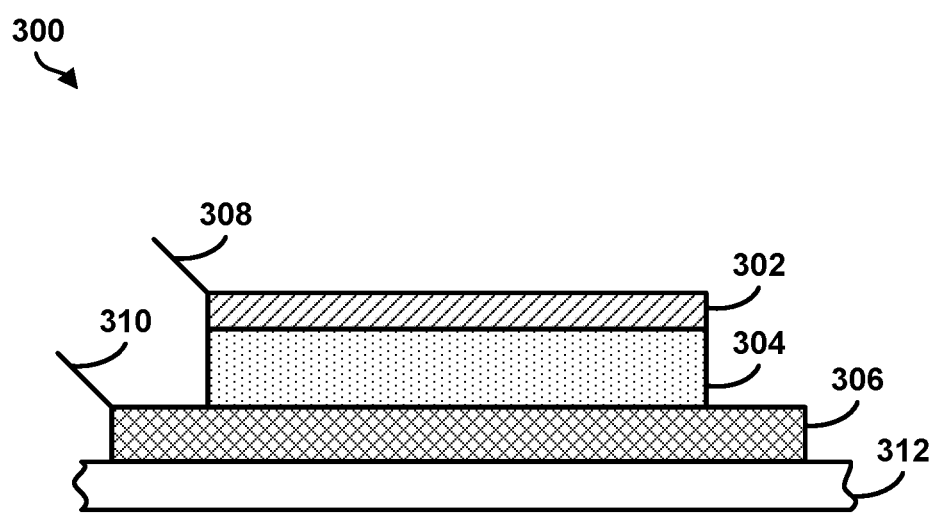
FIG. 3 illustrates an example capacitive element, according to an example embodiment.

FIG. 3 illustrates an example capacitive element 300, according to an example embodiment. The capacitive element 300 may represent one of the capacitive elements 202 of FIG. 2. As shown in FIG. 3, the capacitive element 300 includes a top conductive layer 302, a dielectric substrate 304, and a bottom conductive layer 306 functioning as a common ground plane. A measurement lead 308 is coupled to the top conductive layer 302, and a ground plane lead 310 is connected to the bottom conductive layer 306. The capacitive element 300 is further shown attached to a surface 312 of a structure.

In one example, the top conductive layer 302 and the bottom conductive layer 306 may be metallic layers. The dielectric substrate 304 is positioned between the top conductive layer 302 and the bottom conductive layer 306, and may be a plastic, such as a liquid crystal polymer. As shown in FIG. 3, a size of the dielectric substrate 304 is the same as a size of the top conductive layer 302. Alternatively, in another example, the dielectric substrate 304 may extend beyond the dimensions of the top conductive layer 302 or have a smaller area than the area of the top conductive layer 302 (not shown). The bottom conductive layer 306 extends beyond the dimensions of the dielectric substrate 304. For instance, the bottom conductive layer 306 may extend beneath multiple capacitive elements of an array of capacitive elements.

Figure 4:
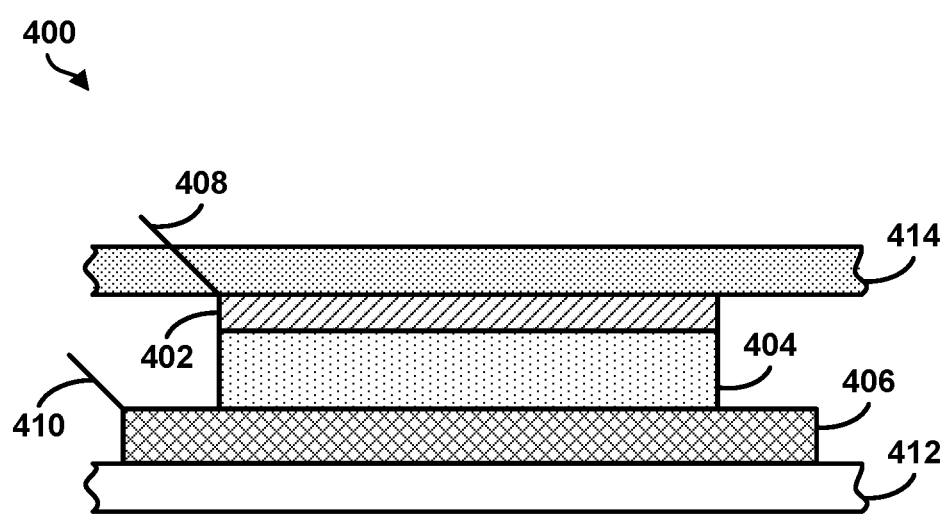
FIG. 4 illustrates another example capacitive element, according to an example embodiment.

FIG. 4 illustrates another example capacitive element 400, according to an example embodiment. Like the capacitive element 300 of FIG. 3, the capacitive element 400 includes a top conductive layer 402, a dielectric substrate 404, a bottom conductive layer 406, a measurement lead 408, and a ground plane lead 410. However, unlike the capacitive element 300 of FIG. 3, the capacitive element 400 is attached to an inner layer 412 of a structure, with the capacitive element 400 covered by an outer layer 414 of the structure (i.e., the capacitive element 400 is positioned between the outer layer 414 and the inner layer 412). In one example, the outer layer 414 may be a protective layer, such as a painted layer or other coating. The measurement lead 408 protrudes through the outer layer 414.

Figure 5:
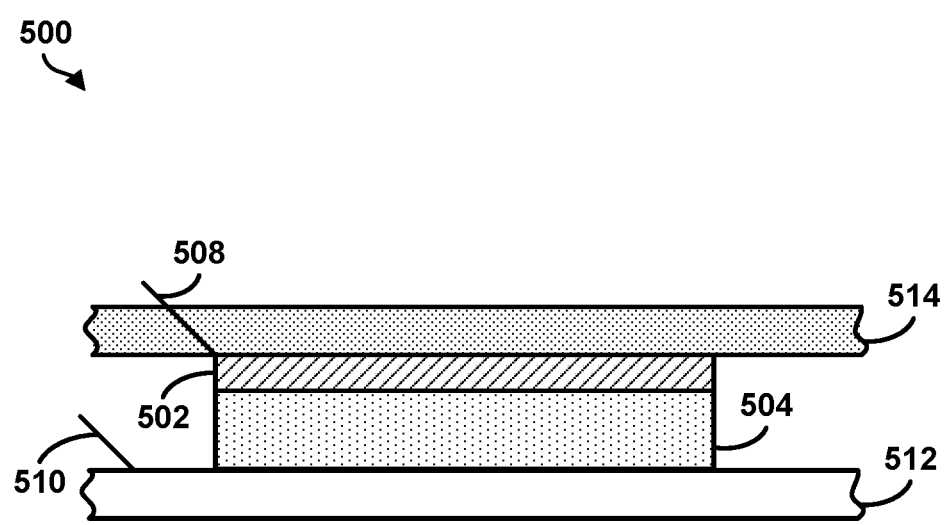
FIG. 5 illustrates still another example capacitive element, according to an example embodiment.

FIG. 5 illustrates still another example capacitive element 500, according to an example embodiment. Like the capacitive element 400 of FIG. 4, the capacitive element 500 includes a top conductive layer 502 and a dielectric substrate 504, with a measurement lead 508 coupled to the top conductive layer 502. And like the capacitive element 400 of FIG. 4, the capacitive element 500 is attached to an inner layer 512 of a structure, and beneath an outer layer 514 of a structure. However, the structure of the capacitive element 400 of FIG. 4 differs from the structure of the capacitive element 500 in that the capacitive element 500 does not include a separate bottom conductive layer. Instead, the inner layer 512 itself functions as a bottom conductive layer and common ground plane for the capacitive element 500. Thus, the ground plane lead 510 is coupled to the inner layer 512.

Figure 6:
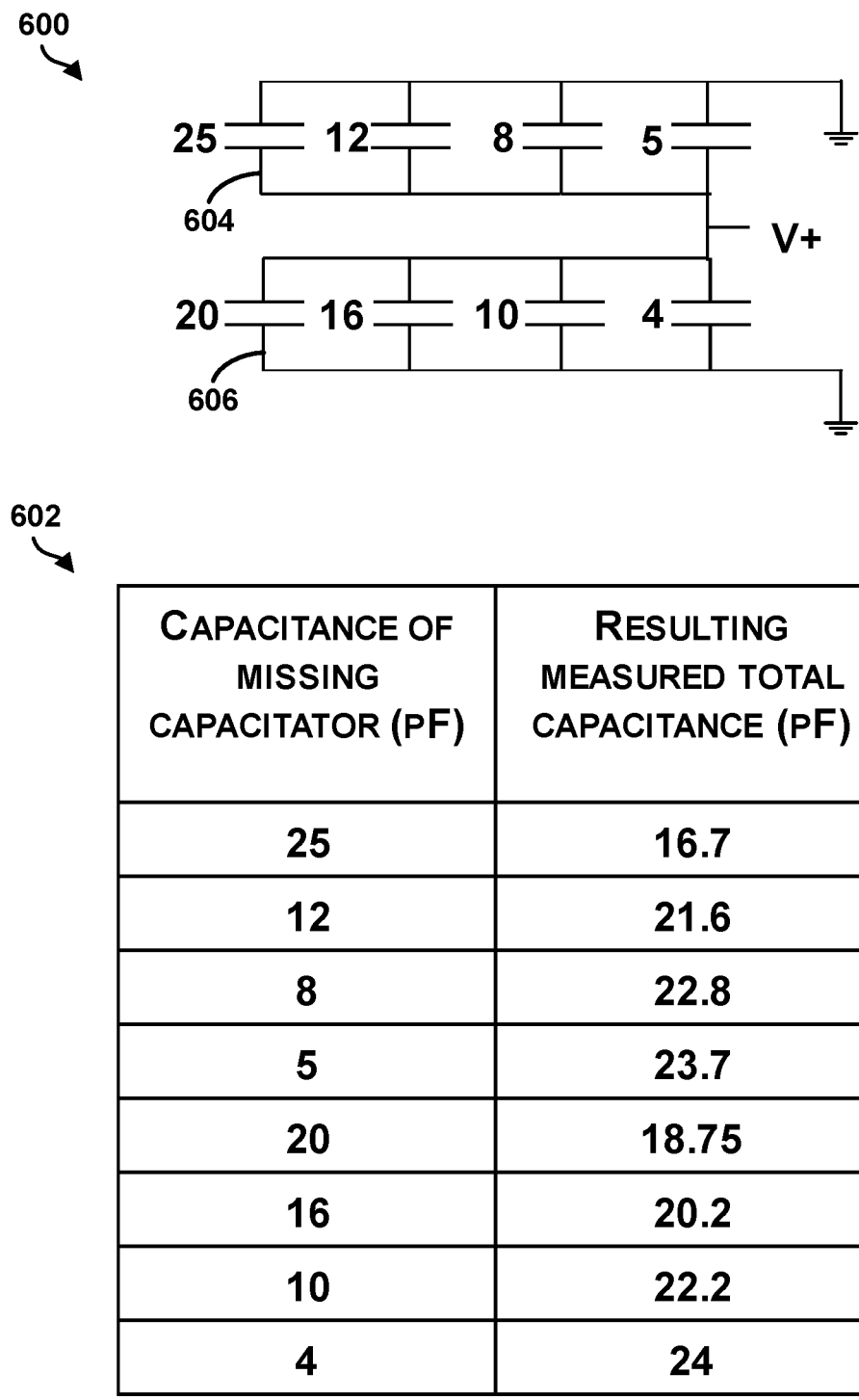
FIG. 6 shows an example circuit diagram and corresponding capacitance variation data structure, according to an example embodiment.

FIG. 6 shows an example circuit diagram 600 and corresponding capacitance variation data structure 602, according to an example embodiment. The circuit diagram 600 may represent a circuit diagram for a sensor having an array of capacitive elements arranged in two rows of four capacitive elements.

As shown in FIG. 6, a first leg 604 of the circuit diagram 600 includes four capacitive elements connected in parallel and having capacitances of 25 picofarads, 12 picofarads, 8 picofarads, and 5 picofarads, respectively. Further, a second leg 606 of the circuit diagram 600 includes four capacitive elements connected in parallel and having capacitances of 20 picofarads, 16 picofarads, 10 picofarads, and 4 picofarads, respectively. The top leg 604 is connected in series with the bottom leg 606.

The equivalent capacitance of multiple capacitive elements connected in parallel is the sum of the individual capacitances of the multiple capacitive elements. Thus, the equivalent capacitance of the first leg 604 is 50 picofarads and the equivalent capacitance of the second leg 606 is also 50 picofarads. The equivalent capacitance of two capacitive elements connected in series is the product of the individual capacitances of the two capacitive elements divided by the sum of the individual capacitances. Thus, the equivalent capacitance of the first leg 604 and the second leg 606 is (50*50)/(50+50), or 25 picofarads. The baseline total capacitance for the circuit diagram 600 is therefore 25 picofarads.

In line with the discussion above, a sensor having an array of capacitive elements corresponding to the circuit diagram 600 may be attached to a structure. If the structure is damaged, a particular capacitive element of the capacitive elements may exhibit a capacitance variation. The capacitance variation may be significant enough for a measurement device to ascertain which of the capacitive elements is exhibiting the capacitive variation.

By way of example, the measurement device may use the capacitance variation data structure 602 to determine a particular capacitive element that is exhibiting a capacitance variation. As shown in the first row of the capacitance variation data structure 602, if the capacitive element having a capacitance of 25 picofarads is damaged or an area of a structure beneath the capacitive element is damaged such that the capacitance of the capacitive element reduces to approximately zero picofarads, the baseline total capacitance may reduce from 25 picofarads to 16.7 picofarads. Thus, when the measurement device measures a total capacitance of 16.7 picofarads, the measurement device may refer to the capacitance variation data structure 602 to determine that the capacitive element having a capacitance of 25 picofarads is damaged. The example configuration shown in the circuit diagram 600 of FIG. 6 is not meant to be limiting. In other examples, an array of capacitive elements may include a single leg of a capacitive elements arranged in series. Alternatively, an array of capacitive elements may include a single leg of capacitive elements arranged in parallel. Other configurations are also possible.

In addition, the measurement device may use a map that maps capacitive elements to positions within the sensor to determine which area of the sensor corresponds to a location of the damage. For instance, the map may indicate that the capacitive element having a capacitance of 25 picofarads is located in an upper left corner of the sensor, and the measurement device may refer to the map to determine that the capacitive element exhibiting the capacitance variation is in the upper left corner of the sensor. In one example, the capacitive elements may be arranged in rows and columns, and the map may indicate respective row and column numbers corresponding to each capacitive element.

An operator may interpret an indication of the position of the capacitive element within the sensor to pinpoint an area where a structure is damaged. For instance, the operator may interpret the fact that the capacitive element is located in the upper left corner of the sensor to mean that an area of the structure beneath the upper left corner of the sensor is damaged.

The capacitance values in the circuit diagram 600 are provided as examples and are not meant to be limiting. In some cases, the variations between capacitance values may be more pronounced. For instance, capacitive elements may have capacitances ranging from 50 picofarads to 1000 picofarads. With such an arrangement, the variations in total capacitance may be more dramatic when one of the capacitive elements exhibits a capacitance variation, such that it is easier to identify which particular capacitive element is exhibiting a capacitance variation.

Figure 7:
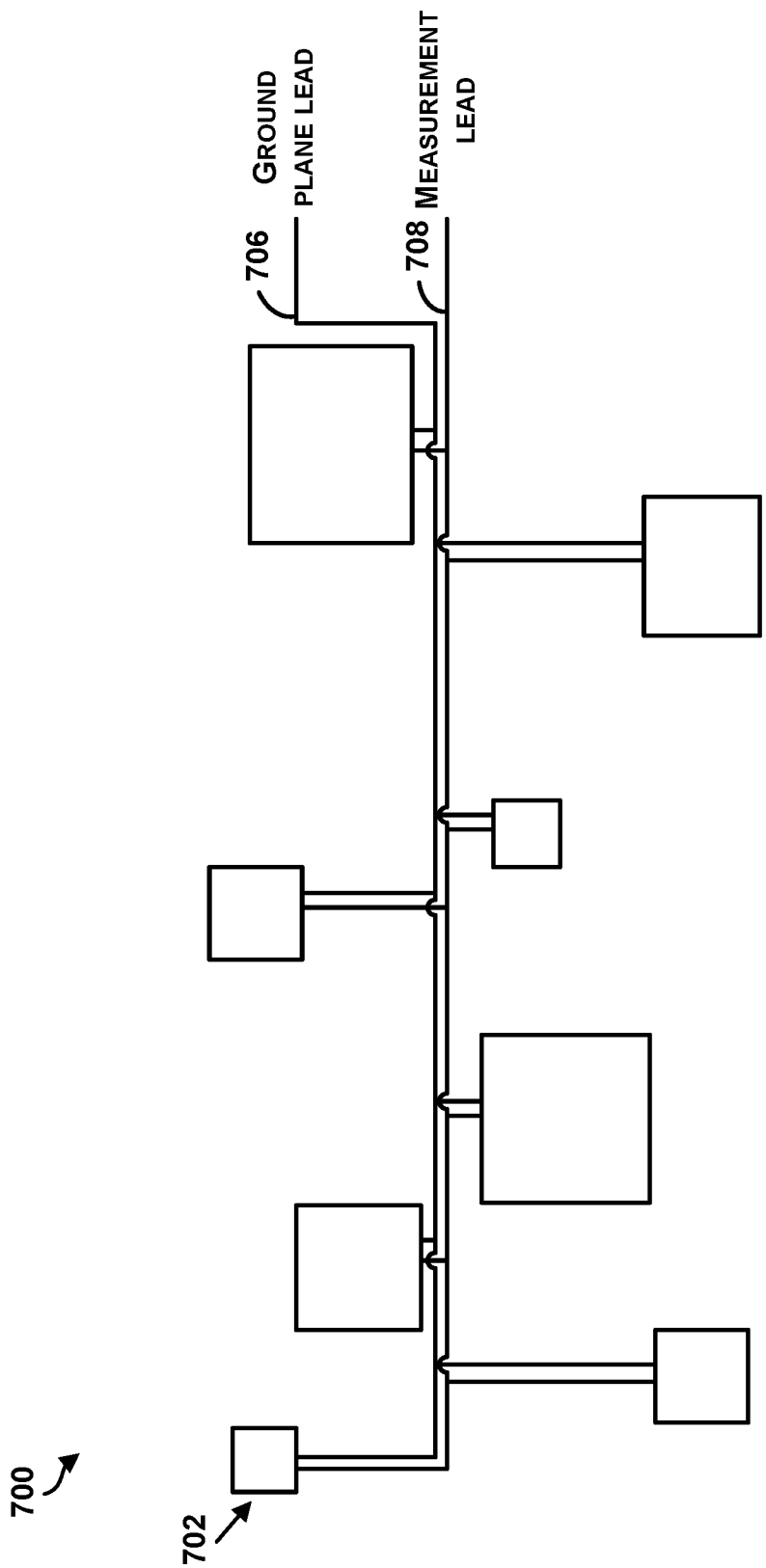
FIG. 7 shows another example sensor, according to an example embodiment.

FIG. 7 shows another example sensor 700, according to an example embodiment. Like the sensor 200 of FIG. 2, the sensor 700 may represent the flexible sensor 104 of FIG. 1. And like the sensor 200 of FIG. 2, the sensor 700 includes an array of capacitive elements 702, a ground plane lead 706, and a measurement lead 708. The sensor 700 of FIG. 7 differs from the sensor 200 of FIG. 2, however, in that the sensor 700 of FIG. 7 does not include a common ground plane. Instead, the ground plane lead 706 is coupled to each of the capacitive elements 702.

In one example, there may be isolated ground planes beneath one or more of the capacitive elements 702, and the ground plane lead 706 may be coupled to the isolated ground planes. Additionally or alternatively, one or more of the capacitive elements 702 may be interdigitated capacitive elements having a first electrode that is interdigitated with a second electrode, and the ground plane lead may be coupled to the second electrode of each of the capacitive elements.

Figure 8:
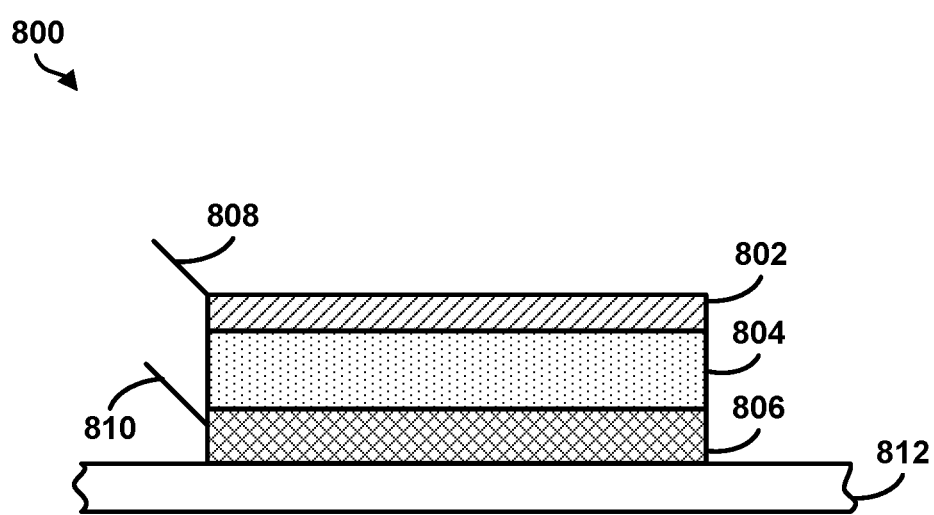
FIG. 8 shows another example capacitive element, according to an example embodiment.

FIG. 8 shows another example capacitive element 800, according to an example embodiment. In particular, FIG. 8 shows a capacitive element 800 having an isolated ground plane that functions as a bottom conductive layer 806 for the capacitive element 800. The capacitive element 800 may represent one of the capacitive elements 702 of FIG. 7. Like the capacitive element 300 of FIG. 3, the capacitive element 800 includes a top conductive layer 802, a dielectric substrate 804, a measurement lead 808, and a ground plane lead 810. And like the capacitive element 300 of FIG. 3, the capacitive element 800 may be attached to a surface 812 of a structure. The bottom conductive layer 806 differs from the bottom conductive layer 306 of FIG. 3, however, in that the bottom conductive layer 806 does not extend beneath multiple conductive elements. As shown in FIG. 8, the bottom conductive layer 806 does not extend substantially beyond the dimensions of the top conductive layer 802.

Figure 9:
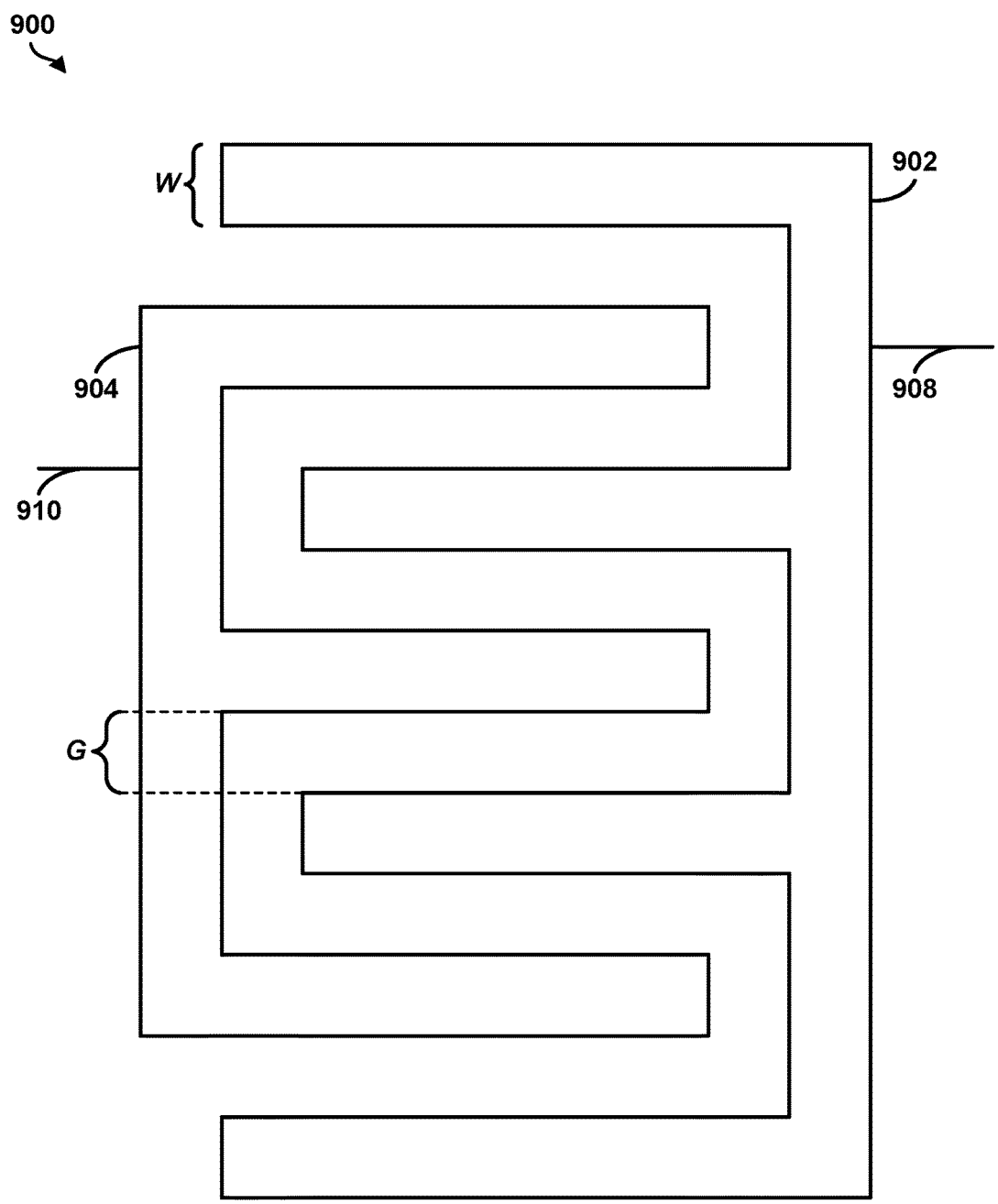
FIG. 9 shows still another example capacitive element, according to an example embodiment.

FIG. 9 shows still another example capacitive element 900, according to an example embodiment. In particular, FIG. 9 shows a capacitive element 900 having a first electrode 902 that is interdigitated with a second electrode 904, with the first electrode 902 coupled to a measurement lead 908 and the second electrode 904 coupled to a ground plane lead 910. The capacitive element 900 may represent one of the capacitive elements 702 of FIG. 7.

In one example, the first electrode 902 and the second electrode 904 may be fabricated on a flexible substrate. The capacitance of the capacitive element 900 may depend on factors such as the width W of the first electrode and the second electrode and the gap G between fingers of the first electrode and fingers of the second electrode. Thus, one of ordinary skill in the art will appreciate that capacitive elements of varying respective capacitances can be created by fabricating capacitive elements with varying widths W and gaps G. For instance, the first electrode may have a first width and the second electrode may have a second width that is different from the first width. Additionally or alternatively, the first electrode may have a first gap and the second electrode may have a second gap that is different from the first gap.

Figure 10:
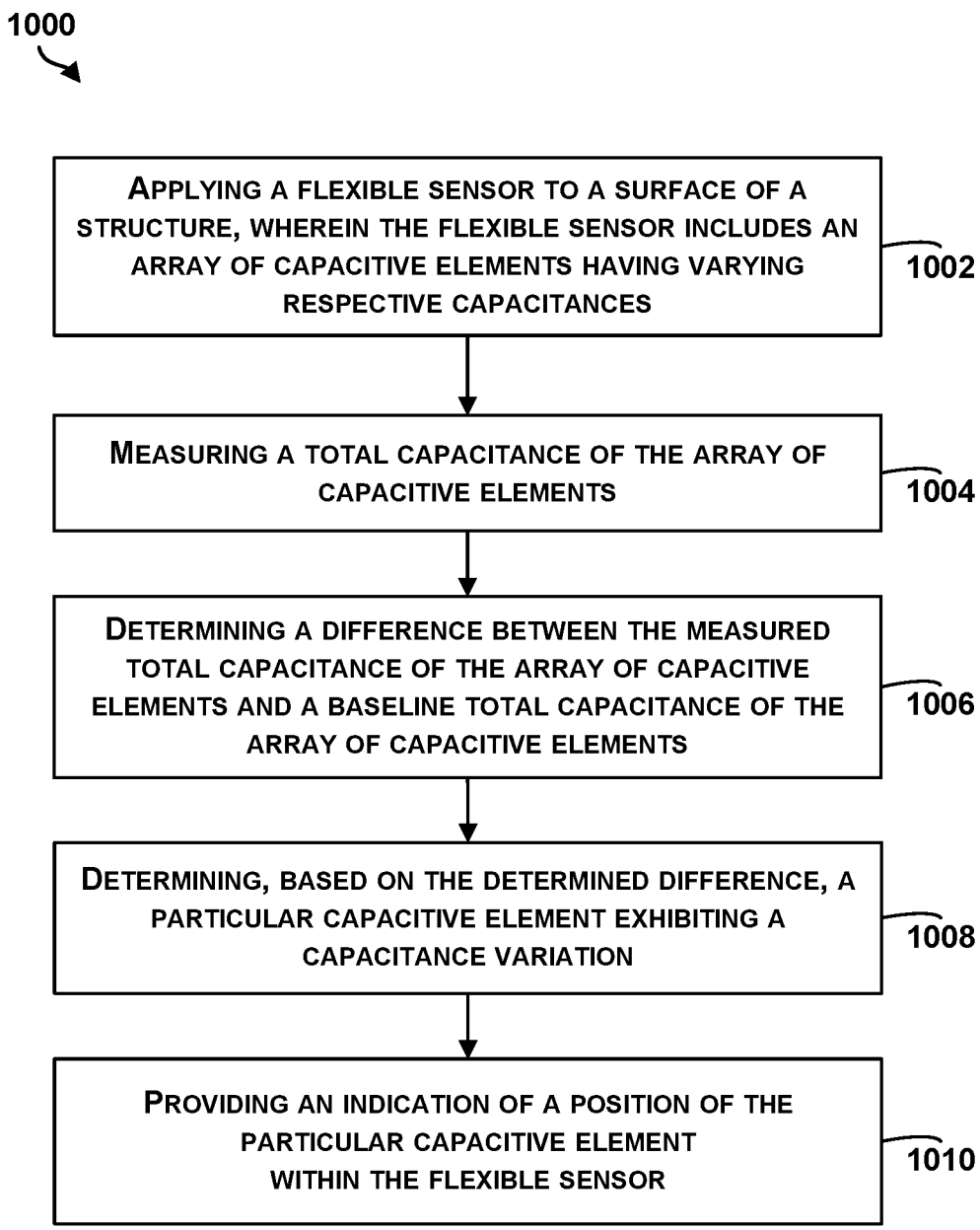
FIG. 10 shows a flowchart of an example method, according to an example embodiment.

FIG. 10 shows a flowchart of an example method 1000 for detecting in-situ structural damage. Method 1000 shown in FIG. 10 presents an embodiment of a method that, for example, could be carried out by a computing device, such as the measurement device 108 (shown in FIG. 1).

It should be understood that for this and other processes and methods disclosed herein, flowcharts show functionality and operation of one possible implementation of present embodiments. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

Referring to FIGS. 1-10, at block 1002, the method 1000 includes applying a flexible sensor 104, 200, 700 to a surface of a structure. The flexible sensor 104, 200, 700 includes an array of capacitive elements 202, 702 having varying respective capacitances. At block 1004, the method 1000 includes measuring a total capacitance of the array of capacitive elements 202, 702. At block 1006, the method 1000 includes determining a difference between the measured total capacitance of the array of capacitive elements 202, 702 and a baseline total capacitance of the array of capacitive elements 202, 702. At block 1008, the method 1000 includes determining, based on the determined difference, a particular capacitive element exhibiting a capacitance variation. And at block 1010, the method 1000 includes providing an indication of a position of the particular capacitive element within the flexible sensor 104, 200, 700.

In line with the discussion above, the capacitive elements of the array of capacitive elements may be structured such that the capacitive elements have varying respective capacitances. Further, the capacitive elements may be arranged positionally within the array of capacitive elements such that a change in total capacitance between a measurement lead and a ground plane lead is indicative of damage to a particular capacitive element at a particular position within the array of capacitive elements.

In one example, the array of capacitive elements may be arranged in rows and columns, and the indication may be a row and column number of the particular capacitive element. In another example, the indication may be an offset from an origin position of the flexible sensor (e.g., a center or a corner).

FIG. 11 shows a flowchart of another example method for use with the method 1000, according to an example embodiment. At block 1012, functions include measuring the baseline total capacitance of the array of capacitive elements. In one example, the measurement device 108 may measure the baseline total capacitance as part of a configuration process after the flexible sensor 104, 200, 700 is applied to or embedded in a structure.

FIG. 12 shows a flowchart of another example method for use with the method 1000, according to an example embodiment. At block 1014, functions include referring to a capacitance variation data structure 602 to determine the particular capacitive element corresponding to the determined difference. The capacitance variation data structure 602 correlates capacitance variations to individual capacitive elements of the array of capacitive elements 202, 702. The function at block 1014 may occur, for example, after block 1006 of FIG. 10 (i.e., after determining the difference between the measured total capacitance and the baseline total capacitance).

FIG. 13 shows a flowchart of another example method for use with the method 1000, according to an example embodiment. At block 1016, functions include wirelessly communicating the indication to another device. This can include wirelessly communicating the indication to another device using the wireless communication node 112, for example. The function at bock 1016 may occur, for example, after the function at block 1010 in FIG. 10 (i.e., after providing the indication of the position of the particular capacitive element within the flexible sensor).

The description of the different advantageous arrangements has been presented for purposes of illustration and description, and is not intended to be exhaustive or limited to the examples in the form disclosed. After reviewing and understanding the foregoing disclosure, many modifications and variations will be apparent to those of ordinary skill in the art. Further, different examples may provide different advantages as compared to other examples. The example or examples selected are chosen and described in order to best explain the principles, the practical application, and to enable others of ordinary skill in the art to understand the disclosure for various examples with various modifications as are suited to the particular use contemplated.

What is claimed is:

1. A system configured to detect in-situ structural damage, the system comprising:
　　an array of capacitive elements, wherein one or more respective capacitive elements of the array of capacitive elements comprise a dielectric substrate and a corresponding top conductive layer, wherein each dielectric substrate is configured to be positioned between the top conductive layer and a common ground plane;
　　a measurement lead coupled to the top conductive layer of each of the one or more respective capacitive elements; and
　　a ground plane lead configured to be coupled to the common ground plane,
　　wherein the capacitive elements of the array of capacitive elements are structured such that the capacitive elements have varying respective capacitances, and
　　wherein the capacitive elements of the array of capacitive elements are arranged positionally within the array of capacitive elements such that a change in total capacitance between the measurement lead and the ground plane lead is indicative of damage to a particular capacitive element at a particular position within the array of capacitive elements.

2. The system of claim 1, wherein the system is configured as a flexible sensor.

3. The system of claim 1, further comprising a bottom conductive layer functioning as the common ground plane for the system, wherein each dielectric substrate is positioned between the bottom conductive layer and the top conductive layer corresponding to the dielectric substrate.

4. The system of claim 3, wherein the system is configured as a flexible sensor.

5. The system of claim 1:
wherein the system is configured to be applied on a surface of a structure with the array of capacitive elements spread out over the surface of the structure such that the change in total capacitance is indicative of damage to a particular position of the surface of the structure, and
wherein the common ground plane comprises a metallic surface of the structure.

6. The system of claim 5, wherein the metallic surface comprises an inner layer of the structure that is beneath an outer layer of the structure.

7. The system of claim 1, wherein the capacitive elements of the array of capacitive elements have varying geometric areas such that the capacitive elements have varying respective capacitances.

8. The system of claim 1, wherein the capacitive elements of the array of capacitive elements are connected as at least two rows of capacitive elements.

9. The system of claim 1, further comprising a measurement device to which the measurement lead and the ground plane lead are coupled, wherein the measurement device is configured to measure the change in total capacitance of the array of capacitive elements.

10. The system of claim 9, further comprising a wireless communication node coupled to the measurement device, the wireless communication node configured to communicate an indication of the total capacitance of the array of capacitive elements to another device.

11. The system of claim 9, further comprising a wireless communication tag coupled to the measurement device, the wireless communication tag configured to store an indication of the total capacitance of the array of capacitive elements.

12. A system configured to detect in-situ structural damage, the system comprising:
an array of capacitive elements;
a measurement lead coupled to each of the capacitive elements of the array of capacitive elements; and
a ground plane lead coupled to each of the capacitive elements of the array of capacitive elements,
wherein the capacitive elements of the array of capacitive elements are structured such that the capacitive elements have varying respective capacitances, and
wherein the capacitive elements of the array of capacitive elements are arranged positionally within the array of capacitive elements such that a change in total capacitance between the measurement lead and the ground plane lead is indicative of damage to a particular capacitive element at a particular position within the array of capacitive elements.

13. The system of claim 12, wherein one or more respective capacitive elements of the array of capacitive elements comprise a dielectric substrate positioned between a corresponding top conductive layer and a corresponding bottom conductive layer, wherein the measurement lead is coupled to the top conductive layers of each of the one or more respective capacitive elements, and wherein the ground plane lead is coupled to the bottom conductive layer of each of the one or more respective capacitive elements.

14. The system of claim 12, wherein each of one or more respective capacitive elements of the array of capacitive elements comprises a first electrode that is interdigitated with a second electrode, wherein the measurement lead is coupled to the first electrode of each of the one or more respective capacitive elements, and wherein the ground plane lead is coupled to the second electrode of each of the one or more respective capacitive elements.

15. The system of claim 12, wherein the system is configured to be applied on a surface of a structure with the array of capacitive elements spread out over the surface of the structure such that the change in total capacitance is indicative of damage to a particular position of the surface of the structure.

16. The system of claim 12, wherein the capacitive elements of the array of capacitive elements have varying geometric areas such that the capacitive elements have varying respective capacitances.

17. A method for detecting in-situ structural damage, the method comprising:
applying a flexible sensor to a surface of a structure, wherein the flexible sensor comprises an array of capacitive elements having varying respective capacitances;
measuring a total capacitance of the array of capacitive elements;
determining a difference between the measured total capacitance of the array of capacitive elements and a baseline total capacitance of the array of capacitive elements;
determining, using a computing device and based on the determined difference, a particular capacitive element exhibiting a capacitance variation; and
providing an indication of a position of the particular capacitive element within the flexible sensor.

18. The method of claim 17, further comprising measuring the baseline total capacitance of the array of capacitive elements.

19. The method of claim 17, wherein determining, based on the determined difference, the particular capacitive element exhibiting the capacitance variation comprises:
referring to a capacitance variation data structure to determine the particular capacitive element corresponding to the determined difference, wherein the capacitance variation data structure correlates capacitance variations to individual capacitive elements of the array of capacitive elements.

20. The method of claim 17, wherein providing the indication of the position of the particular capacitive element within the flexible sensor comprises wirelessly communicating the indication to another device.

* * * * *